United States Patent [19]

Boguslaski et al.

[11] 4,238,195
[45] Dec. 9, 1980

[54] FLUORESCER-LABELED SPECIFIC BINDING ASSAYS

[75] Inventors: Robert C. Boguslaski; Robert J. Carrico, both of Elkhart, Ind.

[73] Assignee: Miles Laboratories, Inc., Elkhart, Ind.

[21] Appl. No.: 4,580

[22] Filed: Jan. 18, 1979

[51] Int. Cl.³ ................ G01N 33/50; G01N 21/76; G01N 21/64
[52] U.S. Cl. ................ 23/230 B; 252/408; 422/61; 424/8; 424/12; 435/7; 435/8; 435/810; 23/915
[58] Field of Search ................ 23/230 B; 424/8, 12; 435/7, 8, 810; 422/61; 252/408

[56] References Cited

U.S. PATENT DOCUMENTS

| | | | |
|---|---|---|---|
| 3,689,391 | 9/1972 | Ullman | 204/159 |
| 3,720,760 | 3/1973 | Bennich | 424/1 |
| 3,992,631 | 11/1976 | Harte | 250/365 |
| 3,996,345 | 12/1976 | Ullman | 424/12 |
| 3,999,948 | 12/1977 | Deindoerfer | 23/230 B |
| 4,014,745 | 3/1977 | Fletcher | 435/8 |
| 4,020,151 | 4/1977 | Bolz | 424/1.5 |
| 4,025,310 | 5/1977 | Bolz | 23/230 B |
| 4,036,946 | 7/1977 | Kleinerman | 424/8 |
| 4,058,732 | 11/1977 | Wieder | 250/461 B |
| 4,104,029 | 8/1978 | Maier | 23/230 B |
| 4,115,699 | 9/1978 | Mizuta | 250/461 B |
| 4,150,949 | 4/1979 | Smith | 435/7 |
| 4,160,818 | 7/1979 | Smith | 424/8 |
| 4,161,515 | 7/1979 | Ullman | 424/8 |

FOREIGN PATENT DOCUMENTS 858722 3/1978 Belgium .
2716276 10/1977 Fed. Rep. of Germany .
2716515 10/1977 Fed. Rep. of Germany .

OTHER PUBLICATIONS

J. Am. Chem. Soc. 88:3604 (1966)–Rauhut et al I.
Accounts of Chem. Res. 2:80 (1969)–Rauhut et al II.
J. Org. Chem. 33:250 (1968)–Maulding et al.

Primary Examiner—Sidney Marantz
Attorney, Agent, or Firm—Andrew L. Klawitter

[57] ABSTRACT

A specific binding assay method and reagent means for determining a ligand, such as an antigen or antibody, in, or the ligand binding capacity of, a liquid medium which employs a fluorescent substance, i.e., a fluorescer, as a label. The improvement comprises measuring the fluorescer-label by chemically exciting the label and measuring the resulting light emitted thereby. Chemical excitation of the label is preferably accomplished by exposure to a substance, such as a high energy intermediate produced by the reaction between hydrogen peroxide and highly reactive materials such as oxalyl chloride, oxamides and bis-oxalate esters. The assay may follow conventional homogeneous and heterogeneous formats. The improved assay is more convenient than conventional fluorescent binding assays by obviating the need for photogenic excitation of the fluorescent label.

26 Claims, No Drawings

FLUORESCER-LABELED SPECIFIC BINDING ASSAYS

BACKGROUND OF THE INVENTION

1. Field of the Invention

This invention relates to assay methods, and reagent means for use therein, of the homogeneous and heterogeneous specific binding type for determining qualitatively or quantitatively a ligand in, or the ligand binding capacity of, a liquid medium. In particular, the invention relates to an improved fluorescer-labeled specific binding assay.

In conventional specific binding assay techniques, a sample of the liquid medium to be assayed is combined with reagent means of various compositions. Such compositions include a labeled conjugate comprising a binding component incorporated with a label, which labeled conjugate participates with other constituents, if any, of the reagent means and the ligand or ligand binding capacity in the medium under assay to form a binding reaction system producing two species or forms of the labeled conjugate, a bound-species and a free-species. The relative amount or proportion of the labeled conjugate that results in the bound-species compared to the free-species is a function of the presence (or amount) of the ligand or ligand binding capacity to be detected in the test sample.

As an illustration, a conventional competitive binding assay technique for the detection of a specific ligand will now be described. In such a technique, the reagent means would comprise (1) a labeled conjugate in the form of the ligand to be detected (e.g., an antigen or hapten) chemically linked to a label, and (2) a specific binding partner for the ligand (e.g., an antibody). Upon combination of the test sample and the reagent means, the ligand to be detected and the ligand portion (i.e., the binding component) of the labeled conjugate would compete in a substantially nondiscriminating manner for noncovalent binding to the specific binding partner. As a result, either the amount of labeled conjugate that becomes bound to the binding partner (i.e., that which results in the bound-species) or that amount which remains free (i.e., unbound to the binding partner and thus that which results in the free-species) can be measured as a function of the amount of competing ligand present. The amount of labeled conjugate resulting in either species is determined by measuring, i.e., monitoring, the label therein.

Where the labeled conjugate in the bound-species is essentially indistinguishable in the presence of that in the free-species by the means used to monitor the label, the bound-species and the free-species must be physically separated in order to complete the assay. This type of assay is referred to in the art as "heterogeneous". Where the bound-species and free-species forms of the labeled conjugate can be distinguished in the presence of each other, a "homogeneous" format can be followed and the separation step avoided.

2. DESCRIPTION OF THE PRIOR ART

The first discovered type of highly sensitive specific binding assay was the radioimmunoassay which employs a radioactive isotope as the label. Such an assay necessarily must follow the heterogeneous format since the monitorable character of the label is qualitatively unchanged in the free- and bound-species. Because of the inconvenience and difficulty of handling radioactive materials, many new assay systems have been devised using materials other than radioisotopes as the label component, including enzymes, bacteriophages, metals and organometallic complexes, coenzymes, enzyme substrates, enzyme inhibitors, cyclic reactants, organic prosthetic groups, chemiluminescent reactants, and fluorescent molecules.

Those specific binding assays developed thus far which employ a fluorescent label rely upon photogenic excitation of the fluorescer, i.e., excitation of the fluorescer by means of irradiation with light to an energy state at which it emits light. The fluorescer can thus be measured by the resulting total or peak light emitted or some other detectable characteristic of the emitted light, such as its polarization. The requirement of incident light to initiate the measurement of the fluorescer is a quite disadvantageous feature of these prior art fluorescent binding assays. Measurement instrumentation is typically both mechanically and electronically complex in order to cope with the problem of interfering background light from incident radiation.

Other specific binding assays have evolved wherein the label is chemiluminescent, i.e., produces light upon chemical reaction. Incident radiation is not required to initiate the monitoring reaction in these assays, however, the sensitivity of such chemiluminescent binding assays presently known is theoretically limited because the material used as the label is invariably, in the prior art, a consumable reactant in the light producing reaction. Furthermore, the chemiluminescent-based specific binding assays thus far published are generally susceptible to protein quenching of light production.

The state of the art of the aformentioned fluorescent and chemiluminescent binding assays will now be briefly outlined with reference to specific prior art publications.

The basic concept of employing fluorescers as labels in specific binding assays is described in U.S. Pat. No. 3,720,760 which offers fluorescein derivatives, in particular fluorescein isothiocyanate, as a label candidate. Such an assay would employ conventional fluorometric techniques to monitor the label. The fluorescer would be excited by irradiation with light of appropriate wavelength and the fluoresced light, appearing at a different wavelength, measured. Various refinements and improvements of this basic fluorescent binding assay technique have evolved, as represented by the techniques described in U.S. Pat. Nos. 3,992,631; 3,999,948; 4,020,151; 4,025,310; 4,036,946; and 4,058,732. These fluorescent assays are based on a heterogeneous format, that is, the label is measured in the bound- or free-species after their separation.

Certain fluorescent binding assays of the homogeneous type have been conceived whereby the usually disadvantageous separation step can be avoided. One such method, the fluorescence polarization technique, is described in U.S. Pat. No. 4,115,699 and is based on the observation that irradiation with polarized light of certain fluorescer-ligand conjugates when bound by a binding partner (e.g., antibody) results in emission of light which has a different polarization. Thus, the bound and free-species of the labeled conjugate can be effectively distinguished in the monitoring reaction.

Another homogeneous fluorescent binding assay is based on quenching or enhancement of fluorescence upon binding of a fluorescer-ligand conjugate by its binding partner. Examples of these techniques are provided by the descriptions in Belgian Pat. No. 858,722 and German Offenlegungsschriften Nos. 2,716,276 and 2,716,515. A variation of this assay method is described in U.S. Pat. No. 3,996,345 which employs a specific quenching substance as a counterpart to the fluorescer label.

Chemiluminescent binding assays are the subject of U.S. Pat. No. 4,104,029 and U.S. patent applications Ser. Nos. 894,836 and 894,838, filed Apr. 10, 1978, which applications are assigned to the present assignee. As indicated previously, the chemiluminescent-based assays specifically described employ consumable reactants as the label, thereby theoretically limiting sensitivity, and, more significantly, are susceptible to protein quenching.

Of ancillary relevance to the present invention are the descriptions in U.S. Pat. No. 3,689,391; Rauhut et al, *J. Am. Chem. Soc.* 88:3604(1966); Rauhut et al, *Accounts of Chem. Res.* 2:80(1969); and Maulding et al, *J. Org. Chem.* 33:250(1968), relating to the inducement of photochemical reactions in the absence of external light by chemical, thermal or electrical excitation of a chemiluminescent material. Application of such phenomenon to analytical methods is not suggested in these references, which were published prior to the previously mentioned references relating to fluorescent immunoassays, or in the subsequent prior art.

SUMMARY OF THE INVENTION

It has now been found that fluorescer-labeled specific-binding assays can be advantageously monitored without photogenic excitation by employing chemical means to excite the fluorescer label. Accordingly, the present invention provides an improvement in a specific binding assay method for determining a ligand in, or the ligand binding capacity of, a liquid medium, wherein the liquid medium is combined with reagent means including a labeled conjugate comprising a binding component incorporated with a fluorescent label, which combination forms a binding reaction system having a bound-species and a free-species of the labeled conjugate, the amount of said fluorescent label resulting in either of the bound or free-species being a function of the presence or amount of the ligand or ligand binding capacity in the liquid medium, and wherein said label is measured in one or both of the species of the labeled conjugate. The improvement comprises accomplishing the measurement step by chemically exciting the label to cause the same to emit light, and then measuring the light emitted by the excited fluorescer. The fluorescent label is preferably excited by exposure to a substance capable of causing such excitation and light emission, for example by exposure to a high energy intermediate reaction product produced by reaction, in the presence of said label, of hydrogen peroxide and oxalyl chloride, an oxamide, or a bis-oxalate ester. The present assay method may follow any conventional homogeneous or heterogeneous assay technique.

The improved reagent means comprises the reagents appropriate for the binding reaction system which is used and, in combination therewith, the chemical means for producing the high energy substance capable of exciting the fluorescer label, i.e., the plurality of reagents which react to produce the high energy intermediate reaction product. In preferred embodiment, such means include (i) hydrogen peroxide or a conventional chemical system for generating hydrogen peroxide and (ii) oxalyl chloride, an oxamide, or a bis-oxalate ester.

According to the present invention, the monitoring reaction is accomplished in the desired species of the binding reaction system (i.e., in the separated bound or free-species when following a heterogeneous format or in the combined species when following a homogeneous format) by addition of the reagents which chemically react to produce a high energy reaction product capable of transferring energy to the fluorescer label to raise same to an excited state. As the excitation of the fluorescer decreases toward a ground state of energy, energy is emitted in the form of light. As an illustration, hydrogen peroxide and various reactive bis-oxalate esters react to form a high energy intermediate believed to be either 1,2-dioxethanedione or activated carbon dioxide. This intermediate transfers energy to a fluorescer which thereafter emits light with a spectrum essentially similar to its normal fluorescence spectrum. The overall reaction for this illustration would be:

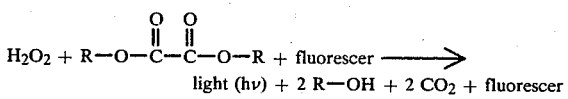

$$H_2O_2 + R-O-\underset{\|}{\overset{O}{C}}-\underset{\|}{\overset{O}{C}}-O-R + \text{fluorescer} \longrightarrow$$
$$\text{light } (h\nu) + 2 R-OH + 2 CO_2 + \text{fluorescer}$$

wherein R represents an organic radical, usually aryl, and $h\nu$ represents electromagnetic radiation in the infra red, visible, or ultraviolet ranges. As shown in the reaction equation, the fluorescer label is neither a consumable reactant nor is it altered chemically in any way during the reaction.

The present invention has several advantages over the prior art fluorescent and chemiluminescent binding assays. One advantage is that relatively simple detection instrumentation may be used, and consequently the necessities of a light source, band filters, and allowances or corrections for scattering of the incident light to the photodetector, all required in fluorometric measurements, are obviated. A further advantage over standard fluorometric detection is that because no incident light is required to initiate light production, all of the light produced, without wavelength restrictions, can be measured. A theoretical advantage over the prior art chemiluminescent binding assays is that of improved sensitivity by reason of the fact that the label does not behave as a consumable reactant. Furthermore, by using multiple fluorescer labels having different maxima for their respective light emissions for the assay of different ligands, a multiple, simultaneous assay format is possible. Furthermore, the present assay is generally free of problematic protein quenching found in prior art chemiluminescent assays.

DESCRIPTION OF THE PREFERRED EMBODIMENTS

In the context of this disclosure, the following terms shall be defined as follows unless otherwise indicated: "ligand" is the substance, or class of related substances, whose presence or the amount thereof in a liquid medium is to be determined; "specific binding partner of the ligand" is any substance, or class of substances, which has a specific binding affinity for the ligand to the exclusion of other substances; "specific binding analog of the ligand" is any substance, or class of substances, which behaves essentially the same as the ligand with respect to the binding affinity of the specific binding partner for the ligand; and "reagent means" is a composition, device or test kit comprising the reagents used to perform the present assay method.

LIGAND

The present assay may be applied to the detection of any ligand for which there is a specific binding partner and, conversely, to the detection of the capacity of a liquid medium to bind a ligand (usually due to the presence of a binding partner for the ligand in the medium). The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Examples of ligands are immunologically-active polypeptides and proteins of molecular weights between 1,000 and 4,000,000, such as antibodies and antigenic polypeptides and proteins, as well as haptens of molecular weights between 100 and 1,500. Representative of such antigenic polypeptides are angiotensin I and II, C-peptide, oxytocin, vasopressin, neurophysin, gastrin, secretin, and glucagon. Representative of antigenic proteins are insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), intrinsic factor, transcobalamin, enzymes such as alkaline phosphatase and lactic dehydrogenase, and hepatitis-associated antigens such as hepatitis B surface antigen ($HB_sAg$), hepatitis B e antigen ($HB_eAg$) and hepatitis B core antigen ($HB_cAg$). Representative of antibody ligands are those antibodies of the IgG, IgE, IgM and IgA classes specific for any of the antigens or haptens herein described. The class of hapten ligands are exemplified by thyroxine, liothyronine, the estrogens such as estriol, prostaglandins, vitamins such as biotin, vitamin $B_{12}$, folic acid, vitamin E, vitamin A, and ascorbic acid (vitamin C), and drugs such as carbamazepine, quinidine, digoxin, digitoxin, theophylline, phenobarbital, primidone, diphenylhydantoin, morphine, nicotine, and so forth.

The liquid medium to be assayed can be a naturally occurring or artificially formed liquid suspected of containing the ligand or a binding capactiy therefor, and usually is a biological fluid or a liquid resulting from a dilution or other treatment thereof. Biological fluids which can be assayed following the present method include serum, plasma, urine, saliva, and amniotic and cerebrospinal fluids. Other materials such as solid matter, for example tissue, can be assayed by reducing them to a liquid form, such as by dissolution of the solid in a liquid or by liquid extraction of the solid.

FLUORESCER

The fluorescer used according to the present invention may be any fluorescent substance, that is, any substance which, upon excitation to a high energy state, such as by illumination or upon exposure to a high energy intermediate reaction product in accordance with the present invention, thereafter radiates or emits light. The phenomenon of fluorescence, as is well known, is the result of changes in the energy state of electrons in the electronic configuration of the fluorescer. In the case of excitation by incident light of a particular energy (i.e., within a particular range of wavelengths) electrons are excited to a high energy state and, upon decay of that energy state to a lower, more stable level, energy is emitted in the form of light. Because of attendent energy loss in forms other than light during the fluorescence, the emitted light is generally of a lower energy and, accordingly, of a longer wavelength than the incident light.

Of the conventional fluorescers, particularly preferred are those having an organic structure which is readily suited to synthetic coupling to a binding component in the particular binding reaction system to be employed so as to form the necessary labeled conjugate. Examples of such preferred fluorescers are lissamine rhodamine B, rhodamine B, fluorescein, 9,10-diphenylanthracene, perylene, rubrene, pyrene, or fluorescent derivatives thereof, such as the isocyanate, isothiocyanate, acid chloride, or sulfonyl chloride derivatives. The fluorescer is coupled to the selected binding component for the assay (such component will usually be the ligand, a specific binding analog of the ligand, or a specific binding partner of the ligand as will be described in detail below) directly or, more usually, through a bridge group such that the desired fluorescent property of the fluorescer-label is retained in the labeled conjugate. As is presently well known in the art, such bridging group usually comprises between 1 and 50, more usually between 1 and 15, carbon atoms or heteroatoms (e.g., nitrogen, oxygen, sulfur, and phosphorus) in the chain. As a chemical group, the bridging group usually has a molecular weight not exceeding 1000 and usually less than 200. The precise chemical structure of the bridging group, the linkages between the fluorescer-label and the binding component, and the respective terminal groups of the bridging group will all depend upon the precise nature of the fluorescer and binding component involved. The synthetic coupling process which forms the fluorescer-labeled binding component (i.e., the labeled conjugate) is well within the skill of the art.

FLUORESCER EXCITATION REAGENTS

The production of high energy intermediate reaction products capable of exciting the fluorescer-label is adequately described in the art. By way of example are offered those intermediates produced by reaction of hydrogen peroxide with oxalyl chloride; oxamides, such as 1,1'-oxalyl-bis-(benzimidazole), N,N'-dimethyl-N,N'-dinitrooxamide, and N,N'-bis-(phenylsulfonyl) parabamate; or bis-oxalate esters, such as bis-(2,4-dinitrophenyl) oxalate, bis-(pentachloro-phenyl) oxalate, bis-(4-nitro-3-trifluoromethylphenyl) oxalate, bis-(4-nitro-2-formylphenyl) oxalate and bis-(pentafluorophenyl) oxalate. Examples of prior art references relating to the excitation of fluorescers by chemical reaction products are the following: U.S. Pat. No. 3,689,491; Rauhut et al, "A Study of Oxalic Ester Chemiluminescent Reactions", United States Department of Commerce, National Technical Information Service Report AD-775,882; Maulding et al, *J. Org. Chem.* 33:250(1968); Rauhut et al, *J. Am. Chem. Soc.* 88:3604(1966); and Rauhut et al, *Accounts of Chem. Res.* 2:80(1969).

As stated previously, the present assay can follow any of the conventional homogeneous or heterogeneous assay techniques. Following are brief summaries of various types of homogeneous and heterogeneous assay techniques that are available.

HOMOGENEOUS ASSAY TECHNIQUES

A homogeneous assay technique, i.e., an assay technique which does not require a physical separation of the bound-species and the free-species, is available where reaction between the binding component in the labeled conjugate and a corresponding binding partner causes a measurable change, either in a positive or a negative sense, in the light emitted by the fluorescer-label upon chemical excitation as described herein. In such a case, the distribution of the fluorescer-label between the bound-species and the free-species can be determined by adding the reagents necessary to form the high energy intermediate directly to the combined species and measuring the light emitted (usually in terms of total light produced or peak intensity). Several manipulative techniques are available for carrying out a homogeneous assay with the two most common techniques being the direct binding and the competitive binding techniques.

In the direct binding technique, a liquid medium suspected of containing the ligand to be detected is contacted with a conjugate comprising the fluorescer-label coupled to a specific binding partner of the ligand, and any change in light emission by the fluorescer-label is assessed. In the competitive binding technique, the liquid medium is contacted with a specific binding partner of the ligand and with a labeled conjugate comprising the fluorescer-label coupled to the ligand or a specific binding analog thereof, and thereafter any change in light emission by the fluorescer-label is assessed. In both techniques, the fluorescer-label is measured by contacting the liquid medium with the reagents which react to produce the high energy intermediate capable of exciting the label. Qualitative determination of the ligand in the liquid medium involves comparing the light emission from assay of the liquid medium to that in liquid media containing known amounts of the ligand.

In general, when following the homogeneous assay technique, the components of the specific binding reaction, i.e., the liquid medium suspected of containing the ligand, the labeled conjugate, and/or a specific binding partner of the ligand, may be combined in any amount, manner, and sequence, provided that the light emission of the fluorescer-label is measurably altered when the liquid medium contains the ligand in an amount or concentration of significance to the purposes of the assay. Preferably, all of the components of the specific binding reaction are soluble in the liquid medium.

Where a direct binding homogeneous technique is used, the components of the binding reaction are the liquid medium suspected of containing the ligand and a quantity of a conjugate comprising the fluorescer-label coupled to a specific binding partner of the ligand. The light emission of the conjugated fluorescer on contact with the liquid medium varies (usually inversely) with the extent of binding between the ligand in the liquid medium and the specific binding partner in the labeled conjugate. Thus, as the amount of ligand in the liquid medium increases, the light emission from the conjugated fluorescer will usually decrease.

Where a competitive binding homogeneous technique is used, the components of the binding reaction are the liquid medium suspected of containing the ligand, a quantity of a conjugate comprising the fluorescer-label coupled to the ligand or a specific binding analog of the ligand, and a quantity of a specific binding partner of the ligand. The specific binding partner is contacted simultaneously or sequentially with the labeled conjugate and the liquid medium. Since any ligand in the liquid medium competes with the ligand or specific binding analog thereof in the labeled conjugate for binding with the specific binding partner, the light emission of the conjugated fluorescer on contact with the liquid medium varies (usually directly) with the extent of binding between the ligand in the liquid medium and the specific binding partner. Thus, as the amount of the ligand in the liquid medium increases, the light emission from the conjugated fluorescer will usually increase.

Determination of the ligand binding capacity of (e.g., the presence of a specific binding partner of the ligand in) a liquid medium can be accomplished by a homogeneous technique by contacting the liquid medium with a conjugate comprising the fluorescer-label coupled to the ligand or a specific binding analog thereof. The light emission of the conjugated fluorescer on contact with the liquid medium varies (usually inversely) with the extent of binding between the binding capacity of the liquid medium and the ligand or analog thereof in the labeled conjugate similarly to the binding in a direct binding technique for determining the ligand as described above.

HETEROGENEOUS ASSAY TECHNIQUES

The use of a fluorescer-label can also be applied to the conventional heterogeneous type assays wherein the bound- and free-species of the labeled conjugate are separated and the quantity of label in one or the other is determined. The reagent means for performing such a heterogeneous assay may take on many different forms. In general, such means comprises two basic constituents, which are (1) a specific binding partner of the ligand, and (2) a labeled conjugate which is normally a labeled form of (a) the ligand, (b) a specific binding analog of the ligand, or (c) the specific binding partner. The binding reaction constituents are combined simultaneously or in a series of additions with the liquid medium to be assayed and with an appropriate incubation period or periods, the labeled conjugate becomes bound to its corresponding competing binding partners such that the extent of binding, i.e., the ratio of the amount of labeled conjugate bound to a binding partner (the bound-species) to that unbound (the free-species), is a function of the amount of ligand present. To follow is a brief description of some of the different heterogeneous binding techniques that may be used in carrying out the method of the present invention.

For the diagrams which are set out hereinafter, the following legend shall apply:

| Symbol | Definition |
| --- | --- |
| L | ligand to be detected in sample |
| Ⓛ | ligand or specific binding analog thereof |
| B | binding partner for the ligand |
| * | label, i.e., fluorescer |
| \| | insoluble phase |
| → | incubation period |
| (sep) | appropriate separation of the bound- and free-species |

-continued

| Symbol | Definition |
|---|---|
| (lim) | limited; present in an amount less than that capable of being bound to the total available binding sites under the selected reaction conditions during the selected incubation period; i.e., the constituent for which the other constituents compete for binding |
| (exc) | excess; present in an amount greater than that capable of being bound by the total available binding sites under the selected reaction conditions during the selected incubation period |

1. Competitive binding heterogeneous formats

L+Ⓛ+B(lim)→+insolubilizing agent for B or Ⓛ
(sep)  (a)

This is the classical competitive binding approach. Examples of insolubilizing agents are specific precipitating antibodies, specific insolubilized antibodies, and, where B or Ⓛ is a proteinaceous material, protein precipitators such as ammonium sulfate, or where B or Ⓛ is a small adsorbable molecule, dextran-coated charcoal. Description of parallel systems can be found in *Biochem. J.* 88:137 (1973) and U.S. Pat. No. 3,839,153.

L+Ⓛ+ ⊢B(lim)→(sep)  (b)

This approach is commonly referred to as the solid-phase technique. Descriptions of parallel radioimmunoassay and enzyme immunoassay techniques can be found in U.S. Pat. Nos. 3,505,019; 3,555,143; 3,646,346; and 3,654,090.

L+B*+ ⊢L(lim)→(sep)  (c)

Reference: U.S. Pat. No. 3,654,090.

L+ ⊢L+B* (lim)→(sep)  (d)

Reference: U.S. Pat. No. 3,850,752.

Further details concerning competitive binding heterogeneous formats can be obtained by reference to Skelley, *Clin. Chem.* 19(2):146–186(1973).

2. Sequential saturation heterogeneous formats

L+B(exc)→+ Ⓛ *(exc)→+insolubilizing agent
for B or Ⓛ * (sep)  (a)

In the sequential saturation technique, some or all the binding sites on B remaining after the first incubation period are bound by the labeled constituent.

L+ ⊢B(exc)→+ Ⓛ *(exc)→(sep)  (b)

Descriptions of parallel radioimmunoassay and enzyme immunoassay techniques can be found in U.S. Pat. No. 3,720,760 and *J. Immunol.* 209:129(1972).

L+B*(exc)→+ ⊢L(exc)→(sep)  (c)

3. "Sandwich" heterogeneous format

L+ ⊢B(exc)→+B*(exc)→(sep)  (a)

In the sandwich technique, some or all of the ligand molecules bound to the insolubilized binding partners are bound by the labeled constituent.
Reference: U.S. Pat. Nos. 3,720,760 and 3,867,517 and Haberman, *Z. Clin. Chem. u. Clin. Biochem.* 8:51–55 (1970).

L+B*(exc)→ ⊢B(exc)→(sep)

This is the so-called "reverse" sandwich technique.
Reference: U.S. Pat. No. 4,098,876.

For further discussion of the parameters involved in conventional heterogeneous assay systems, such as more detailed descriptions of assay formats and alternative separation techniques, reference can be had to *Principles of Competitive Protein-Binding Assays*, ed. Odell and Daughaday, J. B. Lippincott Co. (Philadelphia 1972) and *Radioimmunoassay Methods*, ed. Kirkham and Hunter, Churchill Livingstone (Edinburgh 1971).

It is contemplated that manipulative schemes involving other orders of addition and other binding reaction formats can be devised for carrying out homogeneous and heterogeneous specific binding assays without departing from the inventive concept embodied herein.

The reagent means of the present invention comprises all of the essential chemical elements required to conduct a desired assay method encompassed by the present invention. The reagent means is presented in a commercially packaged form, as a composition or admixture where the compatability of the reagents will allow, in a test device configuration, or as a test kit, i.e., a packaged combination of containers holding the necessary reagents. Included in the reagent means are the reagents appropriate for the binding reaction system desired, always requiring a labeled conjugate as defined hereinbefore. Such binding reaction reagents can include, in addition to the labeled conjugate, a binding partner to the ligand and so forth. Where a heterogeneous binding format is desired, the binding reaction reagents can include an insolubilized reagent or chemical means for rendering either of the bound- or free-species insolubilized.

As an illustration, a typical set of binding reaction reagents for performing a homogeneous competitive binding assay for an antigen ligand would be (1) a fluorescer-labeled form of the ligand or a binding analog thereof and (2) an antibody to the antigen. A typical heterogeneous competitive binding assay set of reagents for an antigen ligand might be (1) a fluorescer-labeled form of the ligand or a binding analog thereof and (2) an insolubilized form of an antibody to the antigen. The very numerous possible permutations of binding reaction reagents and of commercial packaging formats are well within the ordinary skill in the art and are encompassed by the present invention.

In addition to the aforesaid binding reaction reagents, the present reagent means also includes one of the previously described plurality of reagents which react in the presence of the fluorescent label to produce a high energy intermediate reaction product which thereupon excites the label to a high energy state and causes it to emit light. Preferably, such plurality of reagents comprises (i) hydrogen peroxide or any conventional chemical system generating hydrogen peroxide and (ii) oxalyl chloride, an oxamide, or a bis-oxalate ester, the latter two classes of compounds including the preferred species described previously herein.

Of course, the reagent means can include other reagents as are known in the art and which may be desirable from a commercial and user standpoint, such as buffers, diluents, standards, and so forth. In summary, it is to be understood that the reagent means of the present invention can comprise any elements known in the art of the heretofore available specific binding assay reagent means wherein the label is the fluorescer-label of the present invention and such reagent means additionally include one of the above described plurality of reagents for generating the high energy intermediate reaction product.

The present invention will now be illustrated, but is not intended to be limited, by the following examples.

MATERIALS AND METHODS

Reagents

Lissamine rhodamine B was obtained from Pfaltz and Bauer (Stamford, Connecticut, USA), hydrogen peroxide (50%) from Fischer Scientific (Fairlawn, New Jersey, USA), and sisomicin from Schering Corp. (Bloomfield, New Jersey, USA). Bis-(2,4-dinitrophenyl) oxalate was prepared according to the method of Rauhut et al, *J. Amer. Chem. Soc.* 89:6522(1967). Antibody reactive with sisomicin was raised in rabbits immunized with gentamicin coupled to bovine serum albumin [*Nature New Biol.* 239:214(1972)].

Thin-Layer Chromatography

Precoated plates of silica gel (silica gel 60 brand, Merck, Darmstadt, West Germany) were used. The solvent was prepared by vigorously mixing equal volumes of methanol, chloroform and ammonium hydroxide overnight and collecting the resulting lower phase.

Paper Electrophoresis

Electrophoresis was conducted on 28×34 centimeter (cm) sheets of Whatman 3 MM brand paper (Reeve Angel, Clifton, New Jersey, USA) by the hanging strip method described by Williams et al, *Science* 121:829&830(1955). The buffer used was 0.01 molar (M) pyridine-acetate, pH 5.0. A potential of about 17 volts/cm was applied for 5 hours.

Ninhydrin Reaction

Materials with amino residues were detected on thin-layer plates and on electrophoresis paper with the ninhydrin spray reagent of Brenner and Niederweiser, *Methods in Enzymology* 11:39-59(1967).

Purification of Lissamine Rhodamine B

Thin-layer chromatography resolved the commercial lissamine rhodamine B into 15 to 20 red components with the major constituent having an $R_f$ of 0.31. About 7 grams (g) of the crude mixture was stirred with 500 milliliters (ml) of boiling anhydrous ethanol and the resulting mixture was filtered while hot. The filtrate was passed into a 5×50 cm column of Sephadex LH-20 brand gel (Pharmacia Fine Chemicals, Piscataway, New Jersey, USA) in anhydrous ethanol. The column was washed with 6 liters of ethanol and 25 ml fractions were collected. Fractions containing red color were examined by thin-layer chromatography and those containing the lissamine rhodamine B ($R_f$=0.31) were pooled and taken to dryness on a rotary evaporator. This material was purified further by chromatography on a 1 micrometer ($\mu$m) thick layer of silica gel (Quantum, Fairfield, New Jersey, USA). About 120 milligrams (mg) of dye in methanol was applied to a 20×20 cm plate and the chromatogram was developed with the solvent described previously. The heavy red band was scraped from the plate and the dye was eluted from the gel with methanol.

Preparation of Labeled Conjugate (Fluorescer-Labeled Sisomicin)

One hundred milligrams [0.18 millimole (mmol)] of purified lissamine rhodamine B was refluxed in 5 ml thionyl chloride for 45 minutes. The reaction mixture was cooled to room temperature and the thionyl chloride was removed on a rotary evaporator. The residue was dissolved in 20 to 30 ml chloroform and taken to dryness. This process was repeated twice. Thin-layer chromatography resolved this reaction mixture into 15 to 20 components. The dry residue was dissolved in 3 to 4 ml dimethylacetamide and added to a solution containing 44 mg sisomicin (free base) (0.1 mmol) in 5 ml dimethylacetamide and 40 microliters ($\mu$l) triethylamine (0.29 mmol). The reaction mixture stood at room temperature overnight and then the solvent was removed on a rotary evaporator. The residue was stirred with water and the insoluble material was separated by filtration. The water insoluble fraction dissolved in methanol and appeared to have a neutral charge when examined by electrophoresis. The water soluble material was composed of neutral and positively charged red components as well as unreacted sisomicin. It was chromatographed on a 2.5×23 cm column of Sephadex CM 25 brand gel (Pharmacia Fine Chemicals, supra) equilibrated with 0.5 M ammonium formate. The chromatogram was developed with a linear gradient generated with 500 ml 0.5 M ammonium formate and 500 ml 2.5 M ammonium formate. Fractions (13 ml) were collected and the absorbances at 555 nanometers (nm) were measured. Fractions numbered 60-65 were pooled and lyophilized to remove water and ammonium formate. The residue was dissolved in 2 to 3 ml water and purified further by electrophoresis on paper. Three bands migrated toward the cathode at different rates. These were cut out and eluted from the paper with water. The product (sisomicin-fluorescer conjugate) which migrated fastest on electrophoresis was used for further experimentation.

Light-Producing Reactions

A 200 to 500 $\mu$l aliquot of the fluorescer in 0.1 M tris-(hydroxymethyl)-aminomethane hydrochloride (Tris-HCl) buffer, pH 8.0, was dispensed into a 7×70 millimeter (mm) test tube. A designated amount of 50% (v:v) hydrogen peroxide was added to each sample. The reaction tube was placed in a photometer and 2.0 ml of 20 mM bis-(2,4 dinitrophenyl) oxalate was injected from a syringe. Light production was recorded for a 20 second period beginning at the time of the injection.

Light Measurements

Light-producing reactions were conducted in 7×70 mm test tubes mounted above a photomultiplier (type PM 270D from International Light, Newburyport, Mass., USA). A band pass interference filter (Ditric Optics, Marlboro, Mass., USA), with a 10 nm half band width was placed between the reaction tube and the photomultiplier. The wavelength for maximum transmission for the filter was 579 nm. The cover over the reaction tube had an opening covered by a rubber septum. A syringe needle was passed through the septum for injection of a solution of the oxalate ester into the reaction tube. Light production was recorded in terms of the units of the instrument reading.

Heterogeneous Assay Method

Binding reactions between antibody, the sisomicin-fluorescer conjugate and sisomicin were conducted in 0.1 M Tris-HCl buffer, pH 8.0, (400 μl final volume) at room temperature. The conjugate and sisomicin were combined and the antibody was added last. The binding reaction was allowed to proceed for 20 minutes. Then 150 μl of a solution of 500 g/liter Carbowax 6000 brand polyethyleneglycol (BDH Laboratories, Poole, England) in 0.1 M Tris-HCl, pH 8.0 was added and the protein precipitate which formed (including the "bound-species") was sedimented by centrifugation. Three hundred fifty microliter aliquots of the supernatants (the "free-species") were transferred to clean 7×70 mm test tubes. Hydrogen peroxide was added and light measurements were conducted as outlined above.

RESULTS

Measurement of Lissamine Rhodamine B by Light-Production

Addition of the bis-(2,4 dinitrophenyl) oxalate to the reaction mixture containing lissamine rhodamine B and hydrogen peroxide required 2 to 4 seconds. Within 5 to 10 seconds, the light emission reached maximum intensity and by 15 seconds, it was complete. When the oxalate ester was added to hydrogen peroxide without the fluorescer, light was generated with about the same time course described above. Without the interference filter, this light overloaded the photodetector except at the lowest amplification. The interference filter cut out about 99.5% of this background light.

Binding Reactions Between Antibody and the Sisomicin-Fluorescer Conjugate

A fixed level of the sisomicin-fluorescer conjugate was incubated with various levels of antiserum and then the bound and unbound forms of the conjugate were separated as outlined above. The amount of unbound conjugate (free-species) was measured with the light-producing reaction. The light production decreased as the antibody level increased. One hundred microliters of the antiserum appeared to bind 90% of the conjugate. When lissamine rhodamine B was incubated with the same level of antiserum, the light production was diminished by about 20% (Table 1 below). Non-immune rabbit serum also dimished light production by the sisomicin-fluorescer, but the effect was significantly smaller than that observed with the same level of antiserum.

TABLE 1

Antibody Binding of the Sisomicin-Fluorescer Conjugate

| Sisomicin-Fluorescer (nM) | Lissamine Rhodamine B (nM) | Antiserum (μl) | Non-Immune Serum (μl) | Light Production |
|---|---|---|---|---|
| — | — | — | — | 119 |
| — | — | 10 | — | 158 |
| — | — | 100 | — | 160 |
| — | — | — | 10 | 140 |
| — | — | — | 100 | 205 |
| 375 | — | — | — | 919 |
| 375 | — | 5 | — | 851 |
| 375 | — | 10 | — | 670 |
| 375 | — | 20 | — | 580 |
| 375 | — | 50 | — | 485 |
| 375 | — | 100 | — | 241 |
| 375 | — | — | 10 | 865 |
| 375 | — | — | 50 | 745 |
| 375 | — | — | 100 | 796 |
| — | 125 | — | — | 1109 |
| — | 125 | 10 | — | 1142 |
| — | 125 | 100 | — | 895 |
| — | 125 | — | 10 | 1300 |
| — | 125 | — | 100 | 1136 |

Competitive Binding Reactions (Heterogeneous)

Variable levels of sisomicin and a fixed level of the sisomicin-fluorescer conjugate were allowed to react with a limited amount of antibody. Then the amount of unbound conjugate was measured with the light-producing reaction. Light production increased as the sisomicin level increased. At the highest level employed, the light production was 79% of that measured in the absence of the antibody.

Sisomicin could be detected at levels as low as 1.3 μM. The data in Table 2 below demonstrate that the sisomicin-fluorescer conjugate is bound specifically by the antibody.

TABLE 2

Competitive Binding Assay for Sisomicin

| Sisomicin-Fluorescer Conjugate (nM) | Sisomicin (μM) | Antiserum (μl) | Light Production |
|---|---|---|---|
| — | — | — | 250 |
| — | — | 100 | 360 |
| — | 5 | 100 | 370 |
| 375 | — | — | 1830 |
| 375 | 5 | — | 1840 |
| 375 | — | 100 | 580 |
| 375 | — | 100 | 550 |
| 375 | 0.025 | 100 | 530 |
| 375 | 0.050 | 100 | 540 |
| 375 | 0.125 | 100 | 560 |
| 375 | 0.250 | 100 | 550 |
| 375 | 0.625 | 100 | 620 |
| 375 | 1.25 | 100 | 870 |
| 375 | 5.00 | 100 | 1380 |
| 375 | 10.30 | 100 | 1520 |

Binding Reactions Monitored Without Separation of Antibody Bound and Unbound Sisomicin-Fluorescer Conjugate Homogeneous Assay)

Various levels of antiserum were incubated with a fixed level of sisomicin-fluorescer conjugate. Then the reaction mixtures were used in the light-producing reaction without separation of the antibody bound and unbound forms of the conjugate. The results in Table 3 show that the production of light decreased as the antibody level increased. Non-immune rabbit serum had relatively little effect on the light production.

Competitive binding reactions were carried out with variable levels of sisomicin and fixed levels of sisomicin-fluorescer conjugate and antiserum (Table 3 below). Light production by these reaction mixtures was measured without prior separation of bound and unbound forms of the conjugate. Increasing levels of sisomicin led to increased light production although the change in light production was not as great as that observed when the separation step was included.

TABLE 3

Competitive Binding Assay for Sisomicin Monitored Without Separation of Antibody Bound and Unbound Forms of the Sisomicin-Fluorescer Conjugate

| Sisomicin-Fluorescer Conjugate (nM) | Lissamine Rhodamine B (nM) | Sisomicin (μM) | Antiserum (μl) | Light Production |
|---|---|---|---|---|
| — | — | — | — | 140 |
| — | — | — | 100 | 170 |
| — | 125 | — | — | 1310 |
| — | 125 | — | 100 | 930 |
| — | 125 | 25 | 100 | 980 |
| 375 | — | — | — | 910 |
| 375 | — | 5 | — | 860 |
| 375 | — | — | 100 | 610 |
| 375 | — | — | 100 | 640 |
| 375 | — | 2.5 | 100 | 670 |
| 375 | — | 5 | 100 | 680 |
| 375 | — | 12.5 | 100 | 720 |

TABLE 3-continued

Competitive Binding Assay for Sisomicin Monitored Without Separation of Antibody Bound and Unbound Forms of the Sisomicin-Fluorescer Conjugate

| Sisomicin-Fluorescer Conjugate (nM) | Lissamine Rhodamine B (nM) | Sisomicin (μM) | Antiserum (μl) | Light Production |
|---|---|---|---|---|
| 375 | — | 25 | 100 | 800 |

What is claimed is:

1. In a specific binding assay method for determining a ligand in or the ligand binding capacity of a liquid medium,
  wherein said liquid medium is combined with reagent means including a labeled conjugate comprising a binding component incorporated with a fluorescent label, said combination forming a binding reaction system having a bound-species and a free-species of the labeled conjugate, the amount of said fluorescent label resulting in either of said bound-species or said free-species being a function of the presence or amount of said ligand or ligand binding capacity in said liquid medium, and
  wherein said fluorescent label is measured,
  the improvement which comprises measuring said fluorescent label by chemically exciting said label to cause the same to emit light, and then measuring the light emitted by the excited fluorescent label.

2. The method of claim 1 wherein said fluorescent label is excited by exposure to a substance capable, upon such exposure, of causing such excitation and light emission.

3. The method of claim 1 wherein said chemical excitation is produced by carrying out in the presence of said label a chemical reaction, a product of which is a high energy substance from which energy is transferred to said label.

4. The method of claim 3 wherein said substance is the product of the reaction of hydrogen peroxide with oxalyl chloride, an oxamide, or a bis-oxalate ester.

5. The method of claim 3 wherein said substance is the product of the reaction of hydrogen peroxide with oxalyl chloride; an oxamide selected from 1,1'-oxalyl-bis-(benzimidazole), N,N'-dimethyl-N,N'-dinitroxamide, and N,N'-bis-(phenylsulfonyl) parabamate; or a bis-oxalate ester selected from bis-(2,4-dinitrophenyl) oxalate, bis-(pentachlorophenyl) oxalate, bis-(4-nitro-3-trifluoromethylphenyl) oxalate, bis-(4-nitro-2-formylphenyl) oxalate, and bis-(pentafluorophenyl) oxalate.

6. The method of any of claims 1–5 wherein said fluorescent label is lissamine rhodamine B, rhodamine B, fluorescein, 9,10-diphenylanthracene, perylene, rubrene, pyrene, or a fluorescent derivative thereof.

7. The method of claim 1 wherein said fluorescent label is lissamine rhodamine B and is chemically excited by exposure to a high energy intermediate produced by reaction of hydrogen peroxide and a bis-oxalate ester.

8. The method of claim 7 wherein said bis-oxalate ester is bis-(2,4-dinitrophenyl) oxalate.

9. The method of claim 1 wherein said ligand is an antigen or an antibody thereto; a hapten or an antibody thereto; or a hormone, vitamin or pharmacological agent, or a receptor or binding substance therefor.

10. The method of claim 1 of the homogeneous type wherein said fluorescent label is measured in the combined bound-species and free-species of the labeled conjugate.

11. The method of claim 1 of the heterogeneous type wherein said bound-species and said free-species of said labeled conjugate are separated and said fluorescent label is measured in one of the separated species.

12. A test kit for use in determining a ligand in a liquid medium by a specific binding assay method, comprising, in a packaged combination, one or more containers holding
  (1) said ligand, or a binding analog thereof, incorporated with a fluorescent label,
  (2) a binding partner for said ligand, and
  (3) chemical reagents capable of reacting to produce a high energy intermediate which excites said fluorescent label to cause same to emit light.

13. The kit of claim 12 wherein said chemical reagents comprise (i) hydrogen peroxide or a chemical system for generating hydrogen peroxide and (ii) oxalyl chloride, an oxamide, or a bis-oxalate ester.

14. The kit of claim 13 wherein said oxamide is selected from 1,1'-oxalyl-bis-(benzimidazole), N,N'-dimethyl-N,N'-dinitrooxamide, and N,N'-bis-(phenylsulfonyl) parabamate, and said bis-oxalate is selected from bis-(2,4-dinitrophenhyl)oxalate, bis-(phentachlorophenyl) oxalate, bis-(4-nitro-3-trifluoromethylphenyl) oxalate, bis-(4-nitro-2-formylphenyl) oxalate, and bis-(pentafluorophenyl) oxalate.

15. The kit of any of claims 12–14 wherein said fluorescent label is lissamine rhodamine B, rhodamine B, fluorescein, 9,10-diphenylanthracene, perylene, rubrene, pyrene, or a fluorescent derivative thereof.

16. The kit of claim 12 wherein said binding partner is an antibody.

17. The kit of claim 12 wherein said ligand is an antigen or an antibody thereto; a hapten or an antibody thereto; or a hormone, vitamin or pharmacological agent, of a receptor or binding substance 18. The kit of claim 12 wherein said fluorescent label is lissamine rhodamine B and said chemical reagents comprise (i) hydrogen peroxide or a chemical system for generating hydrogen peroxide and (ii) a bis-oxalate ester.

19. The kit of claim 18 wherein said bis-oxalate ester is bis-(2,4-dinitrophenyl) oxalate.

20. A test kit for use in determining the ligand binding capacity of a liquid medium by a specific binding assay method, comprising, in a packaged combination, one or more containers holding
  (1) said ligand, or a binding analog thereof, incorporated with a fluorescent label, and
  (2) chemical reagents capable of reacting to produce a high energy intermediate which excites said fluorescent label to cause same to emit light.

21. The kit of claim 20 wherein said chemical reagents comprise (i) hydrogen peroxide or a chemical system for generating hydrogen peroxide and (ii) oxalyl chloride, a oxamide, or a bis-oxalate ester.

22. The kit of claim 21 wherein said oxamide is selected from 1,1'-oxalyl-bis-(benzimidazole), N,N'-dimethyl-N,N'-dinitrooxamide, and N,N'-bis-(phenylsulfonyl) parabamate, and said bis-oxalate is selected from bis-(2,4-dinitrophenyl) oxalate, bis-(pentachlorophenyl) oxalate, bis-(4-nitro-3-trifluoromethylphenyl) oxalate, bis-(4-nitro-2-formylphenyl) oxalate, and bis-(pentafluorophenyl) oxalate.

23. The kit of any of claims 20–22 wherein said fluorescent label is lissamine rhodamine B, rhodamine B, fluorescein, 9,10-diphenylanthracene, perylene, rubrene, pyrene, or a fluorescent derivative thereof.

24. The kit of claim 20 wherein said ligand is an antigen or an antibody thereto; a hapten or an antibody thereto; or a hormone, vitamin or pharmacological agent, or a receptor or binding substance therefor.

25. The kit of claim 20 wherein said fluorescent label is lissamine rhodamine B and said chemical reagents comprise (i) hydrogen peroxide or a chemical system for generating hydrogen peroxide and (ii) a bis-oxalate ester.

26. The kit of claim 25 wherein said bis-oxalate ester is bis-(2,4-dinitrophenyl) oxalate.

* * * * *